United States Patent [19]
Goldman

[11] Patent Number: 5,922,613
[45] Date of Patent: Jul. 13, 1999

[54] METHOD FOR EVALUATING ESTROGEN DEPENDENT PHYSIOLOGICAL CONDITIONS

[76] Inventor: Dorothee E. F. Goldman, 8881 County Rte. 76, Hammondsport, N.Y. 14840

[21] Appl. No.: 08/913,758

[22] PCT Filed: Mar. 25, 1996

[86] PCT No.: PCT/US96/04007

§ 371 Date: Sep. 22, 1997

§ 102(e) Date: Sep. 22, 1997

[87] PCT Pub. No.: WO96/29606

PCT Pub. Date: Sep. 26, 1996

Related U.S. Application Data

[63] Continuation-in-part of application No. 08/408,966, Mar. 23, 1995, abandoned, and application No. 08/855,590, May 13, 1997.

[51] Int. Cl.$^6$ .......................... G01N 21/77; G01N 33/48; G01N 33/53; G01N 21/00
[52] U.S. Cl. .......................... 436/169; 435/805; 435/806; 435/970; 436/63; 436/64; 436/65; 436/164; 436/817; 436/906
[58] Field of Search ..................................... 435/805, 806, 435/970; 436/63, 65, 64, 164, 169, 817, 906

[56] References Cited

U.S. PATENT DOCUMENTS

| | | |
|---|---|---|
| 3,964,871 | 6/1976 | Hochstrasser . |
| 4,038,485 | 7/1977 | Johnston et al. . |
| 4,320,009 | 3/1982 | Hilton et al. . |
| 4,358,288 | 11/1982 | Goldman . |
| 5,200,325 | 4/1993 | Blatt et al. . |

OTHER PUBLICATIONS

Markaverich. B.M. et al, "Bioflavonoid Interaction With Rat Uterine Type II Binding Sites and Cell Growth Inhibition," J. Steriod Biochem 30(1–6):71–78, 1988.

*Primary Examiner*—Christopher L. Chin
*Assistant Examiner*—Quang N. Phan
*Attorney, Agent, or Firm*—Liniak, Berenato, Longacre & White,LLC

[57] ABSTRACT

A method and apparatus for evaluating estrogen dependent physiological conditions includes a substrate having an anthocyanin pigment applied thereto. The pigment yields a color response indicative of how the body fluid responds to changes in its capacity to absorb free estrogens. The pigment is contacted by the body fluid sample, and the response thereto is connected through color response or optical density measurements to predetermined physiological conditions.

22 Claims, 3 Drawing Sheets

METHOD FOR EVALUATING ESTROGEN DEPENDENT PHYSIOLOGICAL CONDITIONS

CROSS-REFERENCE TO RELATED APPLICATIONS

This application is a rule 371 national phase filing of PCT application No. PCT/US96/04007, which was a continuation-in-part of my then co-pending U.S. patent application Ser. No. 08/408,966, filed Mar. 23, 1995 now abandoned and application Ser. No. 08/855,590, filed May 13, 1997.

FIELD OF THE INVENTION

The present invention is directed to a simple, quick, non-invasive, and easy to use system for evaluating the response of a body fluid to changes in solubility levels for "free" estrogen in order to detect physiological conditions which are estrogen sensitive. The invention permits screening and early identification of estrogen dependent physiological changes and conditions in females, such as follicle growth, growth of endometrial tumors, onset of parturition, and timing of embryo implantation. The system uses anthocyanin pigments which, in the presence of body fluids that contain certain estrogen sensitive components, permit visible color responses to be observed, with those responses correlating with estrogen dependent events.

BACKGROUND OF THE INVENTION

The estrogens to which the invention pertains are called "free" estrogens, and they are known to have hormone effects on certain body functions. Estrogens include a group of steroid hormones essential for normal development and for the healthy functioning of the female reproductive system. Only a small percentage of estrogen (1% of total estrogens in human females) are not chemically bound; unbound estrogens are known as free estrogens. Evaluation of "free" estrogen levels can have diagnostic importance, as observed in the growths of certain estrogen dependent tumors, occurrence of cystic ovaries, and the regulation of possible endometriosis. In some female mammals, changes in concentration of free estrogens are known to occur at the time of embryo implantation, and before the onset of parturition. It is also known that free estrogen levels vary at different times in the life span of a mammal, During fetal development, the concentration of free estrogens is known to increase in the third trimester of pregnancy, due to increased levels of one estrogen form called estriol which is produced by the adrenal glands of the fetus. Prior to delivery, free estrogen levels increase significantly in serum and saliva of different species of pregnant mammals. After delivery, free estrogen levels fall rapidly in the mother, and babies have low levels of free estrogens.

It is also known that estrogen levels increase significantly in girls before they reach puberty. As women age, their ability to produce estrogen decreases after the onset of menopause, and free estrogen levels reach very low levels between 70 and 80 years of age. Free estrogen levels also fall when ovaries are removed from all animal species. Certain activities, such as excessive sports, can also diminish free estrogen levels. Some cases of anovulation have chronic high levels of estrogen, but fail to reach peak levels of estrogen concentration and can result in a condition known as cystic ovaries.

The body regulates the total amount of free estrogen at any given time. An ovulating woman can absorb at least 9 picograms of free estrogen in her saliva. A woman who is about to deliver a baby is able to absorb at least 200 picograms of free estrogens in her saliva. An older menopausal woman will be able to absorb 1–2 picograms of free estrogens in her saliva. In each situation, the body is able to recognize when the capacity to absorb free estrogens is reached. Beyond that point, excess estrogens become bound to other components in the body fluids, thus preventing these excess estrogens from acting as hormones.

The disclosed invention evaluates how a body fluid responds to changes in its capacity to hold or absorb free estrogens; alternatively the invention is useful in evaluating changes in estrogen solubility levels in the body fluid. The invention has many useful applications, and also clinical value as a tool for identifying physiological conditions affected by changes in free estrogen levels. This is especially true in females. It can be used to evaluate how a body fluid responds to changes in the capacity of the body fluid to absorb free estrogens, such as is observed in serum and saliva estrogen levels prior to parturition. It can also be used to evaluate how the body is absorbing estrogens given for therapy, such as in the prevention of osteoporosis or other conditions that benefit from added estrogen. It can evaluate imbalances in certain components sensitive to changes in free estrogen levels, such as observed in endometriosis, and it can track changes in free estrogen levels in the normal development of an individual, such as in the last stages of fetal development, the onset of puberty, and menopause.

It is accordingly an object of the present invention to provide a method and apparatus to easily and rapidly assess for changes in physiological conditions that are estrogen dependent by exposing body fluids, such as saliva, serum, or interstitial fluid, to anthocyanin pigments and to thereafter observe for color responses achieved by the pigments which reflect changes in the response of the body fluid to its free estrogen absorbing capacity of the fluid in order to monitor for estrogen dependent physiological conditions.

SUMMARY OF THE INVENTION

It has now been observed that a simple, non-invasive system using anthocyanin pigments can be used to evaluate estrogen dependent conditions.

In accordance with the invention, there is provided a method to evaluate estrogen dependent physiological changes based upon changes in the capacity of a body fluid to absorb free estrogens which comprises providing a pigmented substrate that is sensitive to changes in a body fluid that are dependent on changes in estrogen solubility. The invention comprises an anthocyanin pigment applied to a substrate to facilitate color change or other optical response in the anthocyanin pigment when contacted with the body fluid, such as saliva, serum, or interstitial fluid. Dilute solutions of calcium salts may also be utilized to yield defined color responses of the pigment that reflect the status of the estrogen dependent physiological event.

In accordance with the invention, there is a method and apparatus to evaluate the color or other optical properties of an anthocyanin pigment which, upon contact with a body fluid, yields a color or other measurable optical response that correlates with the ability of the body to achieve a physiological response to changes in estrogen solubility levels. This color response occurs when saliva or some other body fluid (such as serum or interstitial fluid having pH values between 5.0 and 7.8) is contacted with a defined concentration of certain anthocyanin pigments. If the body fluid already shows maximum responses for free estrogen levels, then the anthocyanin pigment will yield a strong response, generally a blue color, and any added concentrations of free estrogens to the body fluid will cause the blue color to increase in intensity. On the other hand, if the tested body fluid has not reached its maximum ability to respond to changes in free estrogen concentrations, then the observed color response of the anthocyanin pigment is purple, and adding free estrogens causes the color to change from purple to pale purple or pink. Should the body fluid have imbalances in estrogen sensitive components, then the color response is less intense and adding additional estrogen to the body fluid fails to generate an intense blue response. Instead, the color response varies between pale blue, purple, or pink, depending upon what effect the additional soluble estrogen has on the body fluid.

According to another aspect of the present invention, one can quantitatively evaluate whether a given sample of body fluid, such as saliva, is close to its maximum sensitivity to changes in its capacity to absorb free estrogens, by adding controlled amounts of free estrogen and determining how many units are required to cause the color response to change to the intense blue response. Body fluid samples that need small amounts of added estrogens to achieve that color response are close to their limit. Body fluid samples that can absorb large amounts of added estrogen to achieve the color change have larger limits in their capacity to respond to additional free estrogens.

According to a further aspect of the invention, there is also provided a kit to evaluate how the body responds to changes in its capacity to hold free estrogen which includes a first component provided by a substrate, such as transparent sheets, membranes, or strips of glass, acetate, or polyethylene or acrylic or containers or cuvettes made of similar transparent materials, that are coated or sprayed with defined concentrations of anthocyanin pigment, a second component, such as a wick made of cotton, cellulose, absorbent material, or a molecular sieve that can filter components greater than 10,000 Daltons from the body fluid, a third component including dilute solutions of calcium salts preferably in concentrations between $10^{-2}$ to $10^{-3}$ molar, and a fourth component comprising a color comparison chart for comparing color responses produced on the substrate by the pigment to colors that reflect defined responses to changes in the sensitivity of the body fluid to its capacity to hold free estrogens. The kit may optionally include standardized units of a certain estrogen concentration which can be used to evaluate the additional capacity of the body fluid to respond to changes in free estrogen concentration, and a final component comprising written instructions in assisting the user on how to use the kit and interpret the results in order to screen for physiological changes that are estrogen dependent.

The present invention provides many advantages over current technology to evaluate changes in body fluid response systems to changes in the estrogen solubility levels in animals. First, it is non-invasive, and requires small sample amounts to register a color response. Second, it is simple and easy to prepare. Third, it is quick and easy to read.

Current methods to evaluate estrogen levels often need to separate total estrogens into fractions of bound and unbound estrogens. This process involves a series of complicated analytical procedures that are time consuming, frequently requiring several hours. Furthermore, the instrumentation to carry out this process utilizes facilities that are usually available only at research laboratories, clinics, or hospitals. Additionally, many estrogen assays have limited accuracy, and frequently must be repeated.

The disclosed invention offers many benefits to current estrogen evaluation processes. First, this method can be done on site, such as at home, on a farm, or in a zoo, using body fluids that may be obtained in a non-invasive manner. Secondly, small samples of body fluid (between 10 microliters and 150 microliters) are usually sufficient to provide accurate results. Third, this method can be done quickly. Saliva can be exposed to the pigmented substrate of the invention in less than 30 seconds, and the clearly defined color response provides quick feedback about the sensitivity of the body fluid to changes in estrogen solubility levels. A simple, easy to read, evaluation system that responds to changes in estrogen solubility offers new opportunities to permit early screening for physiological conditions that are estrogen dependent.

Specifically an anthocyanin-based system that is sensitive to solubility changes for free estrogens in saliva and serum has practical value in anticipating parturition for livestock and humans. There frequently is a great deal of guess work about whether a pregnant female is in labor. Sometimes parturition is induced when it is too early, and sometimes it is postponed because not enough information is available to indicate the appropriate time. A simple test that measures one way body fluids respond to changes in estrogen activity can improve the guess work and have diagnostic value, as well as help individuals to be better prepared for the actual birthing process.

Also, people who take estrogen therapy might find it beneficial to monitor how much of the estrogen medication is being absorbed or whether the added estrogen is in excess of the levels which they already may absorb. Furthermore, people may wish to know about aging, such as how close they are to puberty, or how quickly they are approaching menopause.

The disclosed pigmented substrate is sensitive to some components that appear to be imbalanced in women who suffer from endometriosis. When estrogen solubility levels increase, the invention yields a color response that correlates with increased occurrence of endometrial tumors. When estrogen solubility levels decrease, the invention yields increasing pale blue color responses that also have lower optical density values. The intensity of the blue color response is markedly diminished in women who suffer from endometrial tumors when compared with optical density values and color responses from women who do not suffer from endometriosis. Such a system offers opportunities to screen women for early detection of possible growths of endometrial tumors, and may also be used to monitor therapy utilized to treat the endometrial tumors.

At present, there are no non-invasive methods available for diagnosing endometriosis. The current method is to do laparoscopy, and to perform biopsies. A simple non-invasive saliva diagnostic that can screen for possible or potential endometriosis avoids painful operations, as well as reducing medical costs.

Additionally, clinics and research institutions may have need for a practical non-invasive system that allows for quick measurement of changes in solubility levels of free estrogens as a routine diagnostic tool to monitor certain aspects of fetal development, or to evaluate other physiologic conditions that appear to be estrogen dependent. Making evaluations in body fluids such as saliva avoids painful blood samples, and potentially reduces infections and other problems that may develop from measuring free estrogen solubility levels based upon blood samples.

A method for evaluating estrogen dependent physiological conditions according to the invention includes the step of providing a body fluid sample. A substrate having an anthocyanin pigment responsive to changes in the estrogen absorption capacity of the body fluid is also provided. The pigment is contacted with the body fluid so that a color response occurs that is reflective of how the body fluid responds to changes in its capacity to absorb free estrogen. The color response of the pigment is then evaluated in order to monitor for estrogen dependent physiological conditions.

A method for indicating endometriosis includes the step of providing a body fluid sample from a female human. A substrate having an anthocyanin pigment responsive to the sensitivity of the body fluid to estrogen absorption is also provided. The body fluid is contacted with the pigment so that a color or optical response indicative of the sensitivity of the body fluid to changes in estrogen absorption may occur. The color response of the pigment is then evaluated in order to monitor for an indication of endometriosis.

A diagnostic apparatus for evaluating estrogen dependent physiological conditions includes a substrate having an anthocyanin pigment operably associated therewith. The pigment is responsive to changes in the estrogen absorption capacity of a body fluid to be evaluated. A collector for a sample of the body fluid is also included. A color chart or other mechanism for evaluating the color response of the pigment after having been contacted by the body fluid sample is provided. The color chart or other mechanism correlates predetermined color responses of the pigment with estrogen dependent physiological conditions.

These and other objects and advantages of the invention will be readily apparent in view of the following description and drawings of the above-described invention.

DESCRIPTION OF THE DRAWINGS

The above and other objects and advantages and novel features of the present invention will become apparent from the following detailed description of the preferred embodiment of the invention illustrated in the accompanying drawings, wherein.

DETAILED DESCRIPTION OF THE INVENTION

Figure 1:
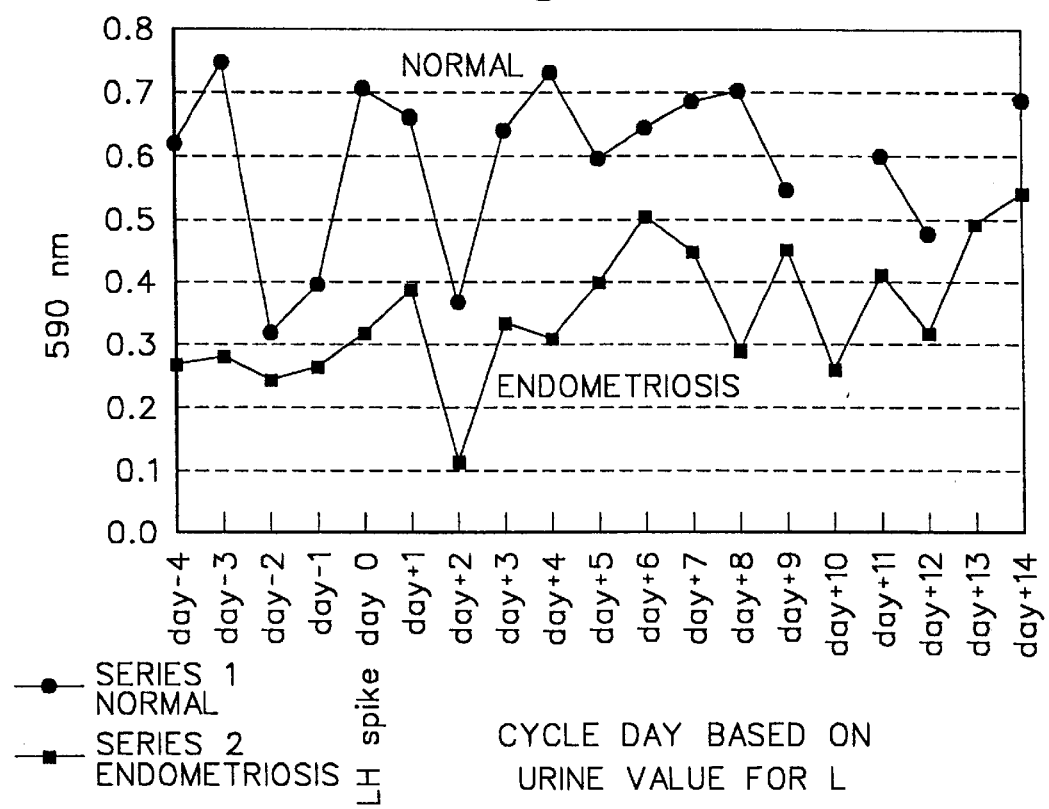
FIG. 1 contains graphs of optical density readings achieved with the invention over a cycle for a woman having endometriosis and one not having endometriosis.

The anthocyanin pigments used in the free estrogen solubility evaluation kit of the present invention have the following general formula. This is based upon an equilibrium ratio of two anhydrobase forms of the anthocyanin pigment as they exist at pH values between 4.0 to 7.5. In this pH range the pigment structure varies between:

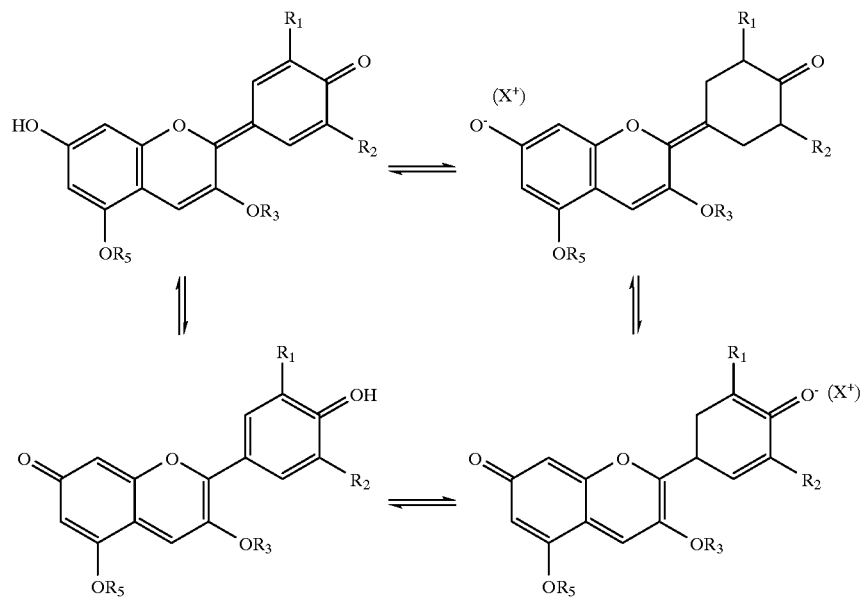

wherein $R_1$ is selected from the group consisting of hydrogen, hydroxy, and C1-C4 alkoxy; $R_2$ is selected from the group consisting of hydrogen, hydroxy, and C1-C4 alkoxy; $OR_3$ is a glycoside selected from the group consisting of glucosides, rutinosides, arabinosides, sophorosides, p-coumaroyl rutinosides, and rhamnosides; $R_5$ is either a hydrogen or a glycoside selected from the group consisting of glucosides; and X is a cation.

The concentration of the pigment preferably falls within the range of $8 \times 10^{-5}$ molar to $1 \times 10^{-3}$ molar. Molar concentrations above $1 \times 10^{-3}$ may not yield definable results, and mclar concentrations below $1 \times 10^{-5}$ may not permit accurate optical density measurements. A molar concentration between $8.0 \times 10^{-5}$ and $2.0 \times 10^{-4}$ gives best results at pH levels between 5.8 and 7.2. The tested medium preferably is between the pH ranges of 5.0 and 7.5, most preferably between 5.8 and 7.2.

The following form of the anthocyanin pigment is favored in the equilibrium ratio when the sensitivity for free estrogen solubility is at its maximum levels:

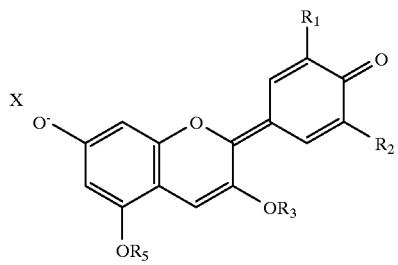

Under these conditions the absorbance values are best read between 500 nm and 620 nm. The maximum absorbance values range between 0.1 and 1.5 for concentrations of anthocyanin pigments between $8 \times 10^{-5}$ molar and $2 \times 10^{-4}$ molar read at 610 nm, and the visible color is blue.

The following form of the anthocyanin pigment is favored in the equilibrium ratio when the sensitivity for free estrogen capacity is not at its maximum levels:

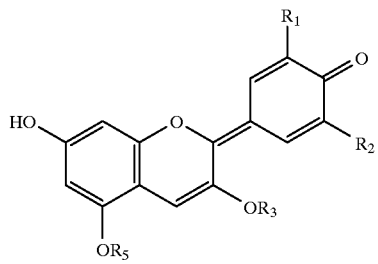

Under these conditions, the maximum absorbance values are best read between 500 nm and 620 nm. The maximum absorbance reading is at 560 nm, and its value rapidly changes from about 0.8 to 0.4, and frequently approaches values of less than 0.1 depending upon the pigment and its concentration. The visible color range is between purple, pink, pale purple, or clear.

It is preferred to use anthocyanin pigments that have glucosides at both the 3 and 5 positions. Some anthocyanin pigments that have a gylcoside on the 7 position do not give intelligible results. The preferred anthocyanin for estrogen solubility determination is malvidin 3,5 diglucoside. Pelargonidin 3,5 diglucoside also gives good results. Petunidin 3,5 diglucoside yields definable results. Preparations from cyanidin 3,5 diglucoside yield well defined results, but shelf life instability needs to be considered.

Sources for Anthocyanins

The anthocyanin pigment of the invention may be obtained from natural plant material. Good sources of cyanidin 3,5 diglucoside are red roses. Pelargonidin may be prepared from geraniums, while petunidin and malvidin may be prepared from grapes.

Procedures for extracting pure pigment crystals are explained in the following journals:

Robinson, A. and Robinson, R. (1929), *Biochemical Journal*, Cambridge University Press, Vol. 23, p. 32–40, and Hrazdina, G., (1970), *Journal of Agricultural Food Chemistry*, Vol. 17, p.243.

The extraction may be validated by comparing the extract against existing methods used to define pure pigments, such as standard Rf procedures for paper chromatography as described in Harborne, *Comparative Biochemistry of Flavonoids*, Academic Press 1967, p. 14 and the reference tables for Rf values on pages 31 to 35. Additionally, one can match prepared samples using a spectrophotometer at the wavelength that gives maximal absorption as a reference indicator for the appropriate anthocyanin. Preparations for pigments prepared in this investigation used both methods.

The procedures for extracting cyanidin 3,5 diglucoside from rose petals is outlined below and methods to test for purity of the extracted pigments are documented in the tables at the end of the procedure.

Pigment Extraction

1. Rose petals from Forever Yours roses from a late bud stage in the floral development of one red rose were press dried and then ground in a food processor.

2. The ground rose tissues were stored in a refrigerated glass jar.

3. 15 mg of dried rose petal tissue was mixed with 1 ml of methanol and then 25 microliters of 0.1 N HCl is added to yield a pH of 5.0.

4. The resulting solution was a clear colorless mixture, with white debris of rose tissue on the bottom.

To test the purity of the anthocyanin pigment, single column paper chromatography measurement for Rf values in a prepared bath of butanol, acetic acid, and water ("BAW") were performed according to the following procedure.

40 ml of butanol was mixed with 10 ml of laboratory grade acetic acid and 50 ml of water added. This was allowed to equilibrate in a sealed glass chromatographic bath at room temperature for 4 hours.

10 microliters of the pigment extract to be tested was inoculated onto a 1 inch by 6 inch strip of Whatman #1 filter paper at 1 inch above the end of the paper. A pencil line was drawn to indicate the extracted pigment's location. This chromatographic paper was placed in the chromatographic bath, so that the tip of strip was about ¼ inch in the BAW solvent.

The BAW solvent was allowed to migrate up the chromatographic paper for 2 hours. At the end of 2 hours, the paper was removed and allowed to dry at ambient conditions. A line was drawn to indicate the front of the solvent.

The dried strip was exposed to ammonia vapor, and the presence of a blue color response reflected the location of the anthocyanin pigment. A pencil line was drawn to indicate this location. This line is known as the Rf line for the anthocyanin pigment.

The distance the anthocyanin pigment traveled is divided by the distance the solvent traveled. This ratio is the Rf value for the anthocyanin pigment. Its value is used to confirm which anthocyanin pigment was extracted from the rose petal by comparing its value to the reference table in Harborne, *Comparative Biochemistry of Flavonoids*, Academic Press, 1967, p. 31–37.

Preparation for cyanidin 3,5 pigments extracted from Forever Yours roses had the following Rf values, as given in Table 1:

TABLE 1

|  | Front | Rf Line | Rf Value |
|---|---|---|---|
| Trial #1 | 3.5 | 1.0 | 0.28 |
| Trial #2 | 2.7 | 0.6 | 0.22 |
| Trial #3 | 2.5 | 0.7 | 0.28 |
| Trial #4 | 2.2 | 0.7 | 0.32 |

Additionally, one can perform a spectral absorbance evaluation. The maximal absorption for rose indicator papers prepared as described in the procedures above was 50% at 537 nm as measured on a reflection absorption spectrophotometer. This absorption value was compared to the standard as stated in Harborne, *Comparative Biochemistry of Flavonoids*, Academic Press, 1967, p.7, which is defined as 536 nm for cyanidin 3,5 diglucoside.

The method to determine whether the body fluid contains maximum levels of soluble free estrogens involves taking defined volumes of the body fluid and exposing same to a given concentration of anthocyanin pigment. This may be done using three different techniques.

1. Measurement of pigment exposed to saliva samples using optical density methods.

The pigment is weighed on a microbalance to achieve a concentration of $1 \times 10^{-3}$ moles. For example, 0.69 mg of malvidin 3,5 diglucoside is mixed with 1 ml methanol. This liquid mixture is aliquoted in 10 microliter portions into wells of an ELISA plate, and then mixed with 90 microliters of saliva. The resulting mixtures are put in a plate reader set at a standard wavelength, such as 590 nm or 560 nm, and absorbance values run.

The procedure for preparing the saliva for optical density measurements is as follows:

1. Whole unstimulated saliva is put into small Eppendorf tubes, 1/day usually in the morning and frozen. No food or liquids are taken within twenty minutes before supplying a sample.

2. After samples have been collected over 30 days and stored in a freezer, then the samples are slowly thawed in an ice bucket.

3. 1000 microliters of the thawed saliva sample is pipetted into a 1.5 ml Eppendorf tube which is centrifuged in a refrigerated centrifuge for 5 minutes at 1100 rpm.

4. 500 microliters of the supernatant are removed and put into a 10 K Nanosep tube (Filtron) and centrifuged in a refrigerated centrifuge at 7000 G at 40° C. for 30 minutes. It has been noted that filtering the saliva samples to include components having a size less than 10,000 Daltons yields more definitive results for optical density measurements than those samples that have larger components and foreign objects, such as food or microbial organisms.

Preparation of the Plate Sample for Optical Density Measurements

1. Clear plastic ELISA plates having 96 wells of up to 150 microliters are used.

2. Three samples of each filtrate are assayed. Each assay consists of 90 microliters of filtered saliva, pipetted into a well, and 10 microliters of $10^{-3}$ molar anthocyanin pigment added to the saliva.

3. The sample is allowed to mix for 15 minutes.

4. The samples are then placed in a Biotek plate reader set at 590 nm. A blank standard 100 microliters of distilled water is used as reference.

5. The date, time, and absorbance value of each sample are noted.

Figure 4:
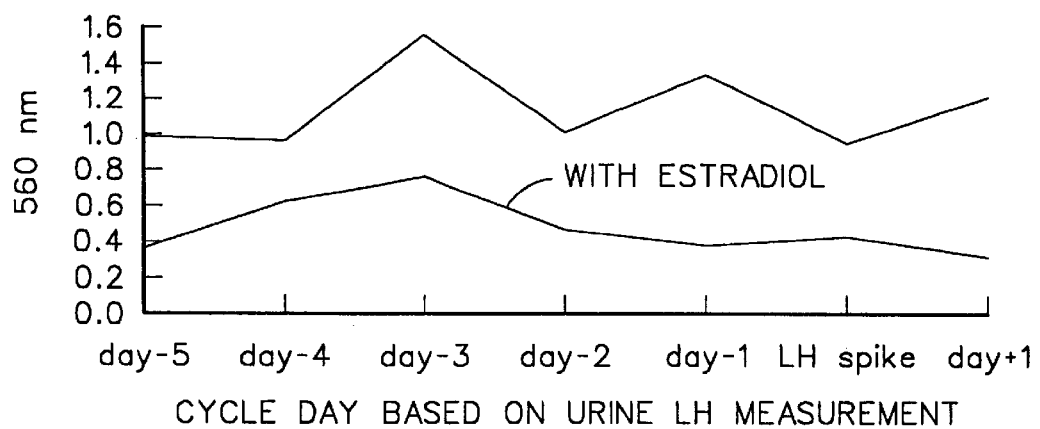
FIG. 4 contains graphs of optical density over time as determined with the invention for whole saliva and whole saliva incubated with 2.7 picogram/milliliter ("pg/ml") estradiol.
Figure 5:
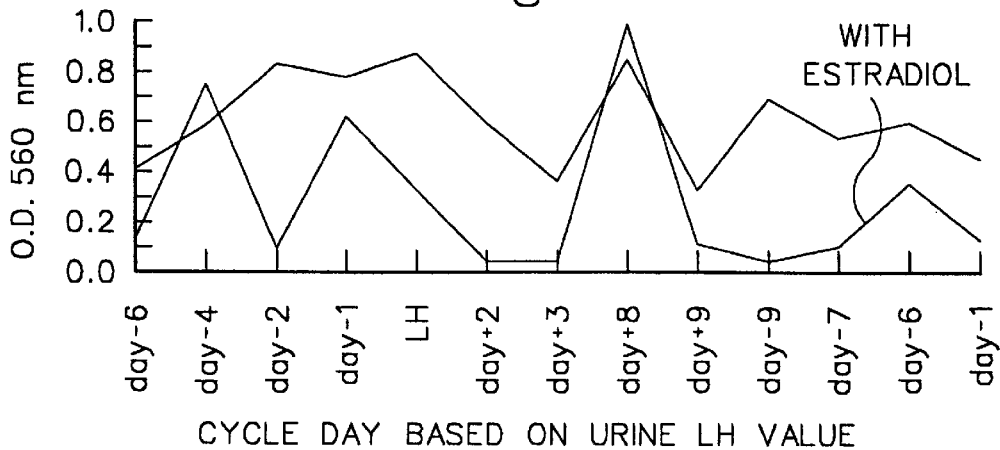
FIG. 5 contains graphs comparing how incubation of 9 pg/ml of estradiol affects optical density values for saliva samples taken from one woman over a period of different days.

Using this procedure it is possible to document what effect the addition of free estradiol has on the ability of the body fluid to respond to changes in estrogen concentration, as best shown in FIGS. 4 and 5.

For example, FIG. 4 demonstrates what effect additional estradiol has on optical density measurements made on saliva samples taken on different days of the menstrual cycle. Whole saliva without added estradiol have higher values than those same samples that have each been incubated in an additional concentration of 2.7 pg/ml. This is also illustrated in Table 2 where color responses are given in addition.

TABLE 2

Optical Density Measurements and Color Responses for Saliva Samples Obtained from Different Cycle Days of a 24 Year Old Woman

| Cycle day based on urine LH measurements | Optical density for saliva not incubated in estradiol | Optical density for saliva incubated in 2.7 pg estradiol | Color response for saliva not incubated in estradiol | Color response for saliva incubated in 2.7 pg estradiol |
|---|---|---|---|---|
| −5 days | 0.982 | 0.355 | blue | purple |
| −4 days | 0.960 | 0.608 | blue | blue-purple |
| −3 days | 1.566 | 0.744 | blue-purple | blue |
| −2 days | 1.005 | 0.449 | purple | purple |
| −1 day | 1.338 | 0.374 | purple | purple |
| LH spike | 0.949 | 0.408 | blue | blue-purple |
| +1 day | 1.214 | 0.295 | blue-purple | purple |
| water | 0.175 |  |  | pale purple |

Measurements made at 560 nm for malvidin 3.5 diglucoside at $4.6 \times 10^{-6}$ M.

FIG. 5 reconfirms these observations by noting what effect the addition of 9 picograms of estradiol has when added to saliva samples taken from different days of the menstrual cycle of another woman. Four days before the documented LH spike (as measured in urine samples), the capacity of the saliva sample was at its maximal level to respond to an additional 9 pg/ml estradiol because the measured O.D. reading for saliva treated with additional 9 pg/ml of estradiol exceeded the O.D. reading for the sample that had not been incubated with this additional estradiol. At three days before the LH spike, the measured O.D. reading for the saliva's response to an additional 9 pg/ml of free estradiol suggests that the sample could easily absorb an additional 9 pg/ml of estradiol. Between two days and one day before the LH spike the ability of the saliva to respond to added amounts of free estradiol gradually became more limited, because the body was now producing its own additional estrogen in preparation for the events that lead to the LH surge. Providing additional estradiol to these samples resulted in less decrease in the measured O.D. values, thus indicating that the capacity of the saliva to respond to additional free estradiol concentration was becoming more limited. After the day of the LH surge, the ability of the saliva to respond to changes in additional estradiol concentrations greatly increased (as observed in O.D. readings that were less than 0.1). This is assumed to be because the actual production of the body's estrogen would be expected to diminish. It is also known that during this period of the menstrual cycle the body produces progesterone, and this process may affect the body fluid's ability to respond to changes in estradiol solubility levels.

After one week after the LH spike on day +8 there was a period of almost no ability to respond to additional estradiol. After this period the ability of the saliva to respond to additional estradiol increases again until the following cycle when the pattern is observed to repeat itself in preparation for a new LH spike. Hence, one can make a quantitative evaluation for the capacity of a body fluid to respond to changes in estrogen absorption by taking the difference in the optical density values for body fluids with added estrogen and without added estrogen. This may be done, for example, with the curves of FIG. 5.

In a preliminary study comparing women with endometriosis to women who did not have endometriosis, color patterns have been observed to be different between women with endometriosis and women who do not have endometriosis, as demonstrated in Tables 3 and 4.

TABLE 3

Saliva Results From One Woman With Endometriosis

| Observed color | Cycle day | O.D. at 590 nm | % retention after 60 min. |
|---|---|---|---|
| light purple | −5 day | 0.331 | 58% |
| light purple | −4 day | 0.295 | 57% |
| light purple | −3 day | 0.3 | 62% |
| light purple | −2 day | 0.258 | 66% |
| pink | −1 day | 0.334 | 66% |
| blue | LH | 0.39 | 69% |
| pink | +1 day | 0.253 | 31% |
| light purple | +2 day | 0.339 | 61% |
| pink | +3 day | 0.274 | 55% |

Measurements made at 590 nm, malvidin 3.5 diglucoside at $1 \times 10^{-3}$ M.

TABLE 4

Saliva Results From Woman With No Endometriosis

| Observed color | Cycle day | O.D. at 590 nm | % retention after 60 min. |
|---|---|---|---|
| blue | −3 day | 0.652 | |
| blue | −1 day | 0.57 | 126% |
| blue | LH | 1.273 | 118% |
| purple | +1 day | 0.581 | 108% |
| purple | +2 day | 0.592 | 138% |
| purple | +3 day | 0.707 | 174% |
| blue | +4 day | 0.561 | 176% |
| blue | +5 day | 0.794 | 93% |
| | +6 day | 0.414 | |
| | +7 day | 0.431 | |
| | +8 day | 0.349 | |

Measurements made at 590 nm, malvidin 3.5 diglucoside at $1 \times 10^{-3}$ M.

Comparisons made between saliva samples from one woman with endometriosis and one woman who does not have endometriosis indicate that each day of the menstrual cycle shows decreased values for absorbency values for saliva samples taken from the woman with endometriosis are illustrated in FIG. 1. Additionally, it is noted that optical density values are inversely correlated with the capacity of the body fluid to respond to additional free estrogens.

Figure 6:
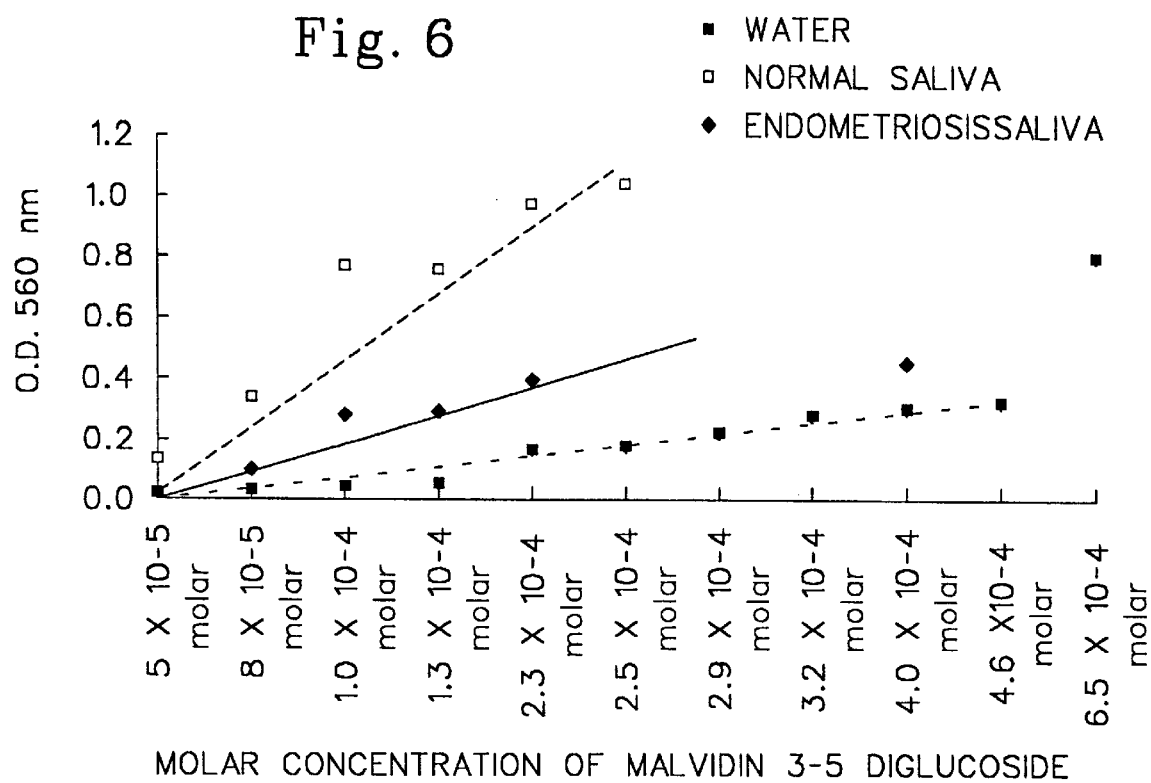
FIG. 6 contains graphs of optical density for water, saliva from a woman having endometriosis, and saliva from a woman not having endometriosis as determined with the invention at differing concentrations of the pigment.

Further evaluation of changes in absorbency values for saliva samples in different molar concentrations of pigment show that absorbency values for increasing concentration of pigment in saliva from a woman with endometriosis showed a slower rate of increased values that those saliva samples from the woman who did not have endometriosis. As the molar concentration of the pigment increased, the absorbency value between the saliva samples from the woman with endometriosis and the woman who did not have endometriosis becomes greater. This is demonstrated in FIG. 6.

Preliminary data of female saliva mixed with the anthocyanin pigment malvidin 3,5 diglucoside suggest that some factor (or factors) in the saliva causes the malvidin 3,5 diglucoside to form blue color complexes which can retain high color absorbance values over a period of several hours for five women with no history of endometriosis. In contrast, saliva samples from two women known to have endometriosis did not yield the intense blue color responses. Instead, the color responses varied from pink to light purple, and had considerably lower absorption values that rapidly degraded within 30 to 60 minutes.

2. Visual interpretation of color response.

Methods using a visible color evaluation system do not necessarily require a filtering process. Distinguishable color readings can be made in samples of unfiltered body fluids exposed directly to a cotton wick or cellulose strip which is then exposed to a transparent substrate holding the pigment. When this method is used to make a determination of the body fluid's sensitivity to changes in solubility levels for free estrogen, it is preferable that the body fluid first come in contact with the cotton wick or cellulose or some other absorbent material, and that the body fluid then be allowed to travel up the wick about 1 mm to 10 mm before coming into contact with the dried pigment applied to a non-cellulose surface, such as acetate, glass, polypropylene, nylon or other synthetic surface. This sequence of steps enhances the clarity of the reaction, making it easier to distinguish between blue and non-blue color responses. The body fluid should be maintained at a temperature between 36 and 98.6° F., preferably at room temperature, while measurements are being made. Heating the body fluid to more than 100° F. degrades its response to changes in the levels of free estrogens.

Preparation of the Pigment Materials for Visual Color Response Evaluation

1. Extracts of 1 microliter of this supernatant containing the dissolved pigment are pipetted onto Whatman 541 filter paper to form round colorless imprints which, upon drying at room temperature, yield a purple circle. For example, pigments extracted from red roses showed with 50% absorbency at 537 nm in the visible spectrum of a reflectance absorbance spectrophotometer.

2. The powdered pigment alternatively can be mixed at a $1 \times 10^{-3}$ molar concentration in methanol, and a clean glass surface is dipped into the pigment mixture. The exposed glass is allowed to dry very rapidly.

Figure 7:
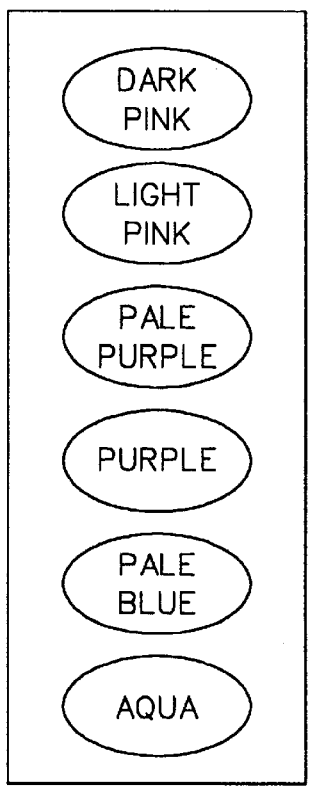
FIG. 7 is a color chart used with the invention.

The substrate is placed on a clean white sheet of paper. Saliva from the mouth is applied to the substrate. Saliva should not be tested until at least 20 minutes after eating, and also saliva flow is very slow in the morning after awakening so that a good reading may not be obtained. The resulting color is then read. There are 6 color categories, as best shown in FIG. 7 for responses to body fluids, as best shown in FIG. 7: aqua, pale blue, purple, pale purple, light pink, and dark pink which refers to no change in the color of pigment spot. Any reading that is in the purple-blue-aqua range does not show significant changes in the capacity to detect changes in estrogen solubility levels. However, a pink response or no development of blue is a sign that the body fluid is able to detect an increase in its capacity to absorb free estrogens.

For example, a pregnant cow that is near term might begin to show pink color responses about two weeks before delivery. However, it is possible that these pink responses are intermittent. It is preferable to follow up with testing for additional pink color responses as a confirmation. Consistent pink color responses that grow progressively paler show that labor may be imminent. A white color response that is very pale and bright indicates that parturition may be within the next six hours. In this way a farmer can determine when it is necessary to prepare for delivery of the calf.

Table 5 shows color responses in a group of five cows.

TABLE 5

| COW | DAY | COLOR RESPONSE |
|---|---|---|
|  |  | Saliva exposed to substrate with anthocyanin pigments extracted from rose pigments |
| COW #328 | −4 | Pink spot went to blue |
|  | −3 | Pink spot went to blue |
|  | −1 | Pink section very pale |
|  | 0 | Delivered |
| COW #329 | −1 | Pale color response |
|  | 0 | Delivered |
| COW #73 | −10 | Blue - stayed blue |
|  | −4 | Blue - slight pink went back to blue |

TABLE 5-continued

| COW | DAY | COLOR RESPONSE |
|---|---|---|
| COW #80 | −7 | Blue - stayed blue |
|  | −1 | Pink |
|  | 0 | Delivered |
| COW #860-S | 0 | Pink |
|  |  | White at −6 hours |
|  |  | Delivered |

Similar color responses have been observed to categorize other situations. Women on birth control pills show no pink color responses because solubility levels for free estrogen do not change much during the time they are taking the pill. Women with case histories of endometriosis show many pink color responses because of imbalances in the response mechanism to this invention. Women who ovulate and have normal menstrual cycles will show a higher frequency of pink color responses in the periods in their cycles when solubility levels for estrogen are expected to change. Table 6 shows examples of these differences.

TABLE 6

| Cycle day | Case #1* | Case #2 | Case #3 | Case #4 | Case #5 | Case #6 | Case #7 | Case #8 | Case #9 | Case #10 |
|---|---|---|---|---|---|---|---|---|---|---|
| −15 |  |  | b | b |  |  |  |  |  | b |
| −14 |  |  | b | b |  |  | b |  |  |  |
| −13 |  |  | b | b |  |  |  |  |  |  |
| −12 | b |  | b | b |  |  | b |  |  |  |
| −11 | b |  | b | b |  |  |  |  |  |  |
| −10 | pb |  | pr |  |  | b | b |  |  | pp |
| −9 | b | b | b | b |  | b | b |  |  | pp |
| −8 | b | pr | b |  | b | b | b |  |  |  |
| −7 | pb | b | b |  | b | b | b |  |  | b |
| −6 | b | b | b |  | b | b | b |  | pp | pk |
| −5 | pk | b | b |  | pb | b | b | pr | pp | pk |
| −4 | b | b | b |  | pb | b | b | pr | pk | pp |
| −3 | pb | pk | pr |  | pb | b | b | pr | pk | pk |
| −2 | pb | pk | b |  | pr | b | b | pr | pk | pk |
| −1 | pb | b | b | pr | pk | b |  |  | pk | pk |
| LH spike | b | b | b | pr | b | b |  | b | b | b |
| +1 | pk | pk | pr | pr | pr | b | b | pk | pp | pp |
| +2 | pk | b | b | b | b | b | b | pp | pp |  |
| +3 | b | b | b | b | b | b | b | p | pp | pp |
| +4 | b | b | b | b | b | b | b | pk | pp | pp |
| +5 | pk | pb | pb | b | pb | b | b | pb | pb |  |
| +6 | b | pb | b |  | b | b |  | cl | pp | pb |
| +7 | b | b | b |  | b |  |  | pb | pk |  |
| +8 | pb | b | b |  | b |  |  | pb | pb |  |
| +9 | pb | pr | b |  | b |  |  | b | pb |  |
| +10 | pk | pr | b |  | b |  |  | pb | pb |  |
| +11 | b | pr | pr |  | b |  |  | pb | pp |  |
| +12 | b | b |  |  | b |  |  | pb |  |  |
| +13 | b | b |  |  |  |  |  | pb |  |  | b = blue
pr = purple
pk = pink
cl = clear
pb = pale blue
pp = pale purple
*Cases #1–5 show results for normal women, cases #6–7 show results for women using birth control pills, and cases #8–10 show results for women with endometriosis.

TABLE 5-continued

| COW | DAY | COLOR RESPONSE |
|---|---|---|
|  | −1 | Purple |
|  | 0 | Delivered |

3. Chromatography Determination

A defined volume of body fluid, between 1 microliter and 10 microliters, is placed onto a piece of chromatographic paper that is in contact with a bead or surface that has 1 microliter to 10 microliters of a given concentration of anthocyanin pigment. The treated chromatographic paper is placed into a chromatographic bath composed of butanol, acetic acid, and water at the ratio of 40:10:50. The saliva sample mixed with the pigment is allowed to migrate up the chromatography paper. The body fluid contacts the anthocyanin pigment, and the combination of the pigment and the body fluid continues migrating with the chromatographic bath fluid up the chromatographic paper at different rates. At the stated time, the exposed chromatographic paper is removed and allowed to dry at room temperature. The dried chromatographic paper is sprayed with a dilute ammonia solution, and measurements are made for the distance the colored pigment spot has moved in relationship to the distance that the chromatography solutions travels. This value is called the Rf value. If the Rf value is greater than 0.4, then the body fluid is approaching its maximum sensitivity to its capacity to absorb more free estrogens. If the Rf value is from 0.1 to 0.36, then the body fluid is far from its maximum capacity to absorb free estrogens.

Protocol for Chromatography

1. A strip of Whatman #1 chromatography paper spotted with 10 microliters of cyanidin 3,5 diglucoside pigment is exposed to 10 microliters of body fluid, such as saliva, and dried. A pencil line is drawn to indicate the location of the pigment spot that has been exposed to the tested body fluid.

2. The treated strip of chromatographic paper is immersed about 1 cm. In a bath of butanol, 1 N acetic acid, water (BAW) having the ratio: 40:10:50.

3. The chromatography paper is left immersed in the closed tank for 20 minutes. After 20 minutes, the paper is removed and a pencil line is drawn to indicate how far the liquid has climbed up the paper. It is dried at room temperature.

4. The chromatography paper is put on top of ammonia vapor to identify the location of the pigment spot that was exposed to the body fluid. A blue aqua color indicates how far the pigment has migrated. A line is drawn on top of the pigment spot.

5. To determine the Rf value for the pigment spot, the ratio of the distance that the pigment spot migrated from the reference line to the distance the liquid traveled from the reference line is calculated. This figure is somewhere between 0 and 1.

Figure 2:
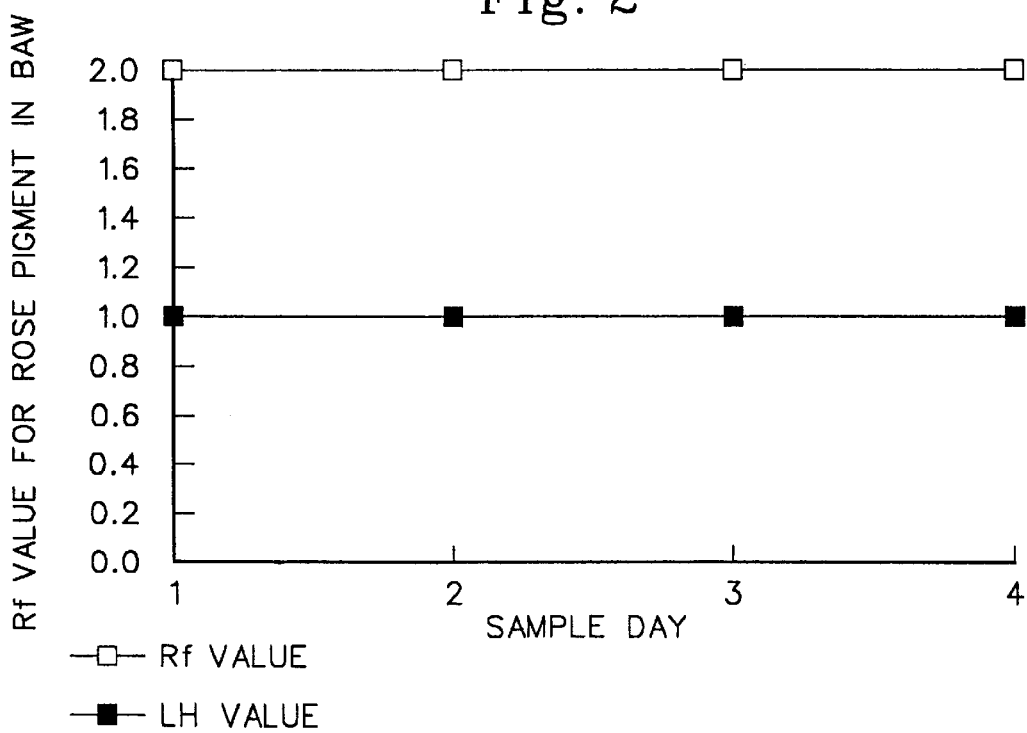
FIG. 2 is a graph of the Rf value for a woman having no ovaries.
Figure 3:
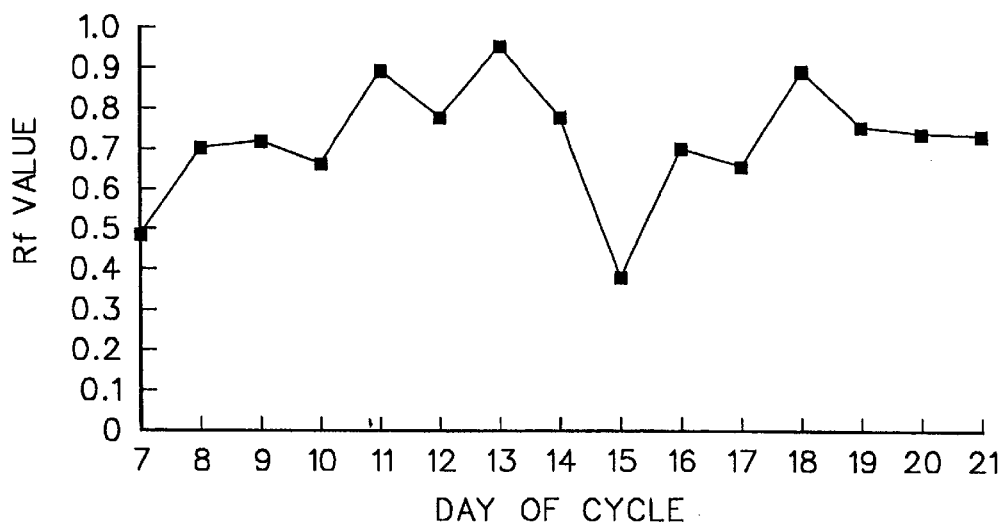
FIG. 3 is a graph of the Rf value over a cycle for an ovulating woman.

Results of chromatography work are shown in the following examples illustrated in FIGS. 2 and 3. Rf values for saliva samples from different days of the menstrual cycle of a woman have decreasing values on the day before the LH spike which was measured using a commercially available kit in urine samples, as best shown in FIG. 3. In contrast, saliva samples from four consecutive days taken from a woman who had her ovaries removed showed no changes in Rf values, as best shown in FIG. 2, suggesting that there are no changes in the ability of the body fluid to respond to changes in estrogen solubility.

Color responses of pigment exposed to saliva samples from different cycle days can be manipulated by adding calcium chloride to the saliva sample or by adding estradiol 17 β. The amount of calcium chloride needed to generate a pink color response depends upon the amount of estradiol 17 β in the saliva sample and the cycle day.

Observational experiments were done to observe what effect calcium chloride and estradiol may have on the pigment color response when added in different amounts to saliva samples taken from different cycle days.

The following Table 7 documents observations of color response to different cycle days and different amounts of calcium chloride and estradiol added.

TABLE 7

| Concentration of calcium chloride added to saliva sample | Saliva from 13 days before LH spike | Saliva from 12 days before LH spike | Saliva from 6 days before LH spike | Saliva from 4 days before LH spike | Saliva from 3 days before LH spike | Saliva from within 24 hours of LH spike | Saliva from within 24 hours after LH spike | Saliva from 4 days after LH spike |
|---|---|---|---|---|---|---|---|---|
| no CaCl$_2$ added | blue | blue | blue | blue | pink | blue | blue | blue |
| more than 1 molar CaCl$_2$ | pink | pink | pink | pink | pink | blue | pink | purple |
| 1 molar CaCl$_2$ | blue | blue | blue | pink | pink | blue | pink | blue |
| $10^{-2}$ molar CaCl$_2$ | blue | no data | no data | purple | pink | blue | blue/purple | blue |
| 1 picogram estradiol and then exposed to $10^{-2}$ molar CaCl$_2$ | | 100 drops of $10^{-2}$ molar CaCl$_2$ needed to generate purple color | many drops of $10^{-2}$ moles CaCl$_2$ added; color stayed blue | 1 drop of $10^{-2}$ molar CaCl$_2$ needed to generate pink color | pink | blue | 20 drops of $10^{-2}$ molar CaCl$_2$ neede to generate purple color | 1 drop of $10^{-2}$ molar CaCl$_2$ needed to generate pink color |
| 10 picograms of estradiol and then exposed to $10^{-2}$ molar CaCl$_2$ | stays blue | 40 drops of $10^{-2}$ molar CaCl$_2$ needed to generate pink color | 30 to 40 drops of $10^{-2}$ molar CaCl$_2$ needed to generate pink color | 1 drop of $10^{-2}$ molar CaCl$_2$ needed to generate pink color | pink | 20 to 40 drops of $10^{-2}$ molar CaCl$_2$ needed to generate pink color 20 to 40 | purple | 1 drop of $10^{-2}$ molar CaCl$_2$ needed to generate purple color |
| 50 picograms of estradiol and then exposed to $10^{-2}$ molar CaCl$_2$ | stays blue | 30 drops of $10^{-2}$ molar CaCl$_2$ needed to generate purple pink color | 20 drops of $10^{-2}$ molar CaCl$_2$ needed to generate pink color | 1 drop of $10^{-2}$ molar CaCl$_2$ needed to generate pink color | pink | 20 drops of $10^2$ molar CaCl$_2$ needed to generate pink color | pink | purple/blue |

Note: All saliva samples that had estradiol added were treated first with the estradiol before the calcium chloride was added. LH values were measured in urine using a commercially available LH kit.

In certain body fluids, such as plasma or saliva of certain animals such as ungulates, it has been observed that it is beneficial to add dilute amounts of calcium salts in order to observe the color changes. After the body fluid has been exposed to the anthocyanin pigment according to the earlier prescribed procedures, then a dilute concentration of a calcium salt is added to the saliva mixture. Preferably the calcium is added in the form of a $1 \times 10^{-3}$ molar solution of calcium chloride ($CaCl_2$). If the resulting color is blue or yields a high absorbance value, then the body fluid is close to or at its maximum level of free estrogen capacity. If the resulting color response is pink, then the capacity to absorb free estrogen is not at its maximum level. This method may be used to evaluate cows for when they might be entering parturition. Other metal salts may be added for similar reasons.

A blue color is the normal response in a cow. This indicates that the cow has maximum sensitivity to its capacity to absorb free estrogens. A pink color indicates that the capacity to absorb levels of free estrogens is increasing. If the response is pink, both before and after the calcium has been added, then this response is an indication that maximum levels of free estrogen have not been reached. The ability to absorb additional estrogen is present. This response occurs before parturition. A pink response suggests that parturition may be soon, while a clear response suggests that parturition will occur within the next six hours.

Uses for Pigmented Substrates

Papers or other substrates according to the invention can be used to determine the degree of synchrony between donors and recipients in embryo transfers. For example, embryo donors and embryo recipients must be in synchrony for patterns of changes in estrogen levels. The invention documents when a hormone injection to cows results in changes in the body fluid sensitivity to estrogen solubility levels. The recipient and donor may thus be monitored for synchronized responses pursuant to the methodology of the invention. The probability for embryo implantation is increased when synchrony is established.

Another application of this invention is to anticipate the onset of labor in pregnant women. About two weeks prior to delivery in full term pregnancies, there is a color shift in the saliva test as used on the cellulose disc treated with rose pigments. During most of pregnancy the color response is blue or purple blue. Two weeks prior to delivery the color response shifts to pink or no blue. This color response remains until the day labor begins when it shifts to a clear, pale blue response about six hours prior to delivery as observed in eight spontaneous deliveries of full term pregnancies. This pattern of color changes has also been observed in induced deliveries which were observed to shift from blue to pale purple within 20 minutes to 2 hours after induction was initiated and then proceed to delivery within 4 to 12 hours after the pale purple color response was observed.

From these examples it can be seen that there are significant, easy to interpret optical changes that occur when anthocyanin pigments come in contact with body fluids that are sensitive to changes in solubility levels for estrogen concentrations. This method to assess changes in a body fluid's sensitivity to changes in free estrogen solubility involves simple and accurate techniques that are easy, inexpensive, and require little time. The system can be applied to many different situations, and can be used in clinic, homes, farms, and zoos where current technology to measure equivalent estrogen levels would not be practical or available. Furthermore this non-invasive simple to use method has broad applications for evaluating estrogen physiological changes that occur in many animals in particular mammals and more particularly females.

While this invention has been described as having a preferred design, it is understood that it is capable of further modifications, uses, and/or adaptations thereof, and following in general the principle of the invention, and including such departures as come within known or customary practice in the art to which the invention pertains.

What is claimed:

1. Method for screening for endometriosis, comprising the steps of:

a) originating with a female human a saliva sample;

b) providing an anthocyanin 3,5-diglucoside pigment at a concentration of between about $8 \times 10^{-5}$ M and $1 \times 10^{-3}$ M at a pH of between about 5.0 and 7.5 responsive to the capacity of the saliva sample to change its free estrogen solubility level;

c) contacting the pigment with the saliva sample and permitting a color response to occur; and d) detecting from the color response of the pigment whether there are imbalances in how the saliva sample responds to changes in its capacity to absorb free estrogen and thereby screening for endometriosis.

2. Method of claim 1, wherein detecting the color response through one of visual perception, optical density determination, and chromatography.

3. Method of claim 2, including the step of:

a) providing a color chart having at least two preselected colors, one color indicative of whether the saliva sample has achieved its maximal capacity to absorb free estrogen; and b) evaluating the color response of the pigment by comparison with the color chart.

4. Method of claim 3, wherein the anthocyanin pigment is selected so as to generate a blue color response to the saliva sample having achieved maximum capacity to absorb free estrogen.

5. Method of claim 2, wherein the color response is detectd by optical measurement, the optical density determination being performed between 500 nm and 620 nm.

6. Method of claim 1, wherein the pigment on the substrate is at a concentration between about $5 \times 10^{-5}$ M to $1 \times 10^{-3}$ M.

7. Method of claim 1, wherein the saliva sample is at a temperature of less than 100° F.

8. Method of claim 1, including the steps of:

adding a known amount of extrogen to the saliva sample after step 6; and repeating step c in order to determine how much of said estrogen must be added to the saliva sample in order to determine the maximum sensitivity for estrogen absorption of the saliva sample.

9. Method of claim 8, wherein the estrogen is estradiol.

10. Method of claim 8, wherein the estrogen is 17 beta estradiol.

11. Method of claim 1, wherein the pigment is malvidin 3,5 diglucoside, petunidin 3,5 diglucoside, cyanidin 3,5 diglucoside, or pelegordinin 3,5 diglucoside.

12. Method of claim 1, wherein the pigment has the following general formula:

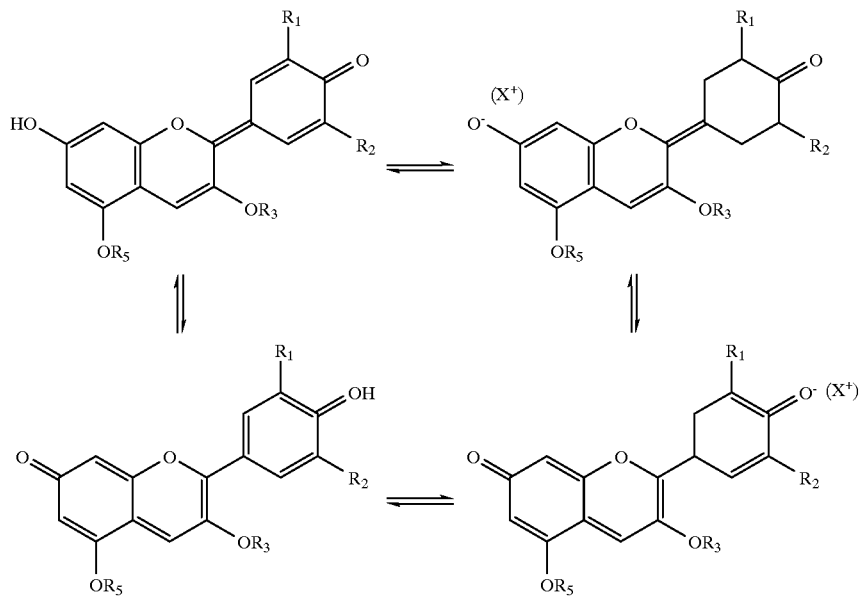

wherein $R_1$ is selected from the group consisting of hydrogen, hydroxy, and $C_1$–$C_4$ alkoxy; $R_2$ is selected from the group consisting of hydrogen, hydroxy, and $C_1$–$C_4$ alkoxy; $R_3$ is a glycoside selected from the group consisting of glucosides, rutinosides, arabinosides, sophorosides, p-cuomaroyl, rutinosides, and rhamnosides; and $R_5$ is a glycoside selected from the group consisting of glucosides, and $X^+$ is a cation.

13. Method of claim 1, wherein a substrate is provided allowing solid phase contact between the saliva sample and the pigment and the substrate is formed from a material selected from the group consisting of transparent glass strip, acetate, polyethylene, acrylic, and cellulose.

14. Method of claim 1, wherein components having a size in excess of 10,000 Daltons are filtered from the saliva sample prior to contact with the pigment.

15. Method of claim 14, wherein the filtering of the saliva sample is performed using a wick formed from the group consisting of cotton, cellulose, absorbent materials, and molecular sieves.

16. Method of claim 1, wherein applying a metal salt with the pigment prior to contacting the pigment with the saliva sample.

17. Method of claim 16, wherein the metal salt is calcium chloride.

18. The method of claim 1, further comprising the step of:
    e) repeating steps b through d of claim 1 with a plurality of saliva samples taken over a selected time interval.

19. The method of claim 18, wherein the saliva samples are taken over a period of at least five days, with at least one sample being taken each day.

20. The method of claim 19, further including the step of:
    f) recording each color response.

21. Method for indicating parturition, comprising the steps of:
    a) originating with a female mammal a saliva sample;
    b) providing an anthocyanin 3,5 diglucoside pigment at a concentration of from about $8 \times 10^{-5}$ M to about $1 \times 10^{-3}$ M at a pH of between 5.0 and 7.5 responsive to the capacity of the saliva sample to change its free estrogen solubility level;
    c) contacting the pigment with the saliva sample and permitting a color response to occur; and
    d) detecting from the color response of the pigment whether the body fluid has achieved its capacity to absorb free estrogen and thereby screening for an indication that parturition may be imminent.

22. Method for indicating synchrony during embryo implantation, comprising the steps of:
    a) originating a plurality of saliva samples, each sample taken from a different female mammal;
    b) contacting each saliva sample with an anthocyanin 3,5 diglucoside pigment at a concentration of from about $8 \times 10^{-5}$ M to about $1 \times 10^{-3}$ M at a pH of between 5.0 and 7.5 responsive to the capacity of the saliva samples to change their free estrogen solubility levels so that a color response occurs; and
    c) evaluating the color response of each saliva sample that has been contacted with the anthocyanin pigment and thereby monitoring for synchrony in color responses between at least two of the female mammals.

* * * * *